United States Patent [19]

Cartwright et al.

[11] Patent Number: 4,918,105
[45] Date of Patent: Apr. 17, 1990

[54] NOVEL COMPOUNDS WITH COLLAGENASE-INHIBITING ACTIVITY, A PROCESS FOR THEIR PREPARATION AND PHARMACEUTICAL COMPOSITIONS IN WHICH THESE COMPOUNDS ARE PRESENT

[75] Inventors: Terence Cartwright, Saint Epain; Romaine Bouboutou-Tello, Arceuil; Yves Lelievre, Tours; Marie-Claude Fournier-Zaluski, Paris, all of France

[73] Assignee: SA Laboratoire Roger Bellon, Neuilly-Sur-Seine, France

[21] Appl. No.: 141,072

[22] Filed: Jan. 5, 1988

[30] Foreign Application Priority Data

Jan. 6, 1987 [FR] France .................. 87 00053

[51] Int. Cl.$^4$ .................. C07C 93/10; A61K 31/16; A61K 31/185; A61K 31/165
[52] U.S. Cl. .................. 514/575; 562/623
[58] Field of Search .............. 260/500.5 H; 514/575; 562/623

[56] References Cited

U.S. PATENT DOCUMENTS

| | | | |
|---|---|---|---|
| 4,105,789 | 8/1978 | Ondett et al. .................. | 424/309 |
| 4,504,492 | 3/1985 | Wilkinson et al. .................. | 514/522 |
| 4,599,361 | 7/1986 | Dickens et al. .................. | 260/500.5 H |
| 4,618,708 | 10/1986 | Rogues et al. .................. | 260/500.5 H |
| 4,743,587 | 5/1988 | Dickens et al. .................. | 200/500.5 H |

FOREIGN PATENT DOCUMENTS

| | | |
|---|---|---|
| 75896 | 4/1983 | European Pat. Off. . |
| 82088 | 6/1983 | European Pat. Off. . |
| 2720996 | 11/1977 | Fed. Rep. of Germany . |

OTHER PUBLICATIONS

Devlin et al, "J. Chem. Soc.", Perkin I, vol. 9, (1975), p. 830–841.

Primary Examiner—J. E. Evans
Attorney, Agent, or Firm—Dennison, Meserole, Pollack & Scheiner

[57] ABSTRACT

The present invention relates to a novel family of chemical compounds possessing a pharmacological activity, in particular a collagenase-inhibiting activity, a process for the production of these compounds and pharmaceutical compositions in which they are present.

According to the invention, these compounds correspond to the general formula:

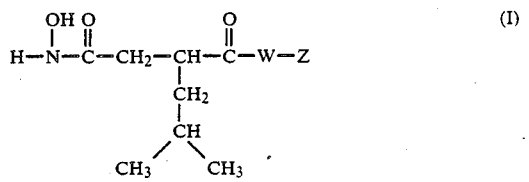

in which:
W represents an amino acid residue selected from the group comprising valine, lysine, norleucine and methionine, and
Z represents an amino radical or an alkylamino radical of which the alkyl part, which contains 1 or 2 carbon atoms, is substituted by a phenyl or trifluorophenyl radical, and also include their diastereoisomers and their addition salts with pharmaceutically acceptable acids.

The invention is applicable especially in the pharmaceutical industry.

10 Claims, No Drawings

NOVEL COMPOUNDS WITH COLLAGENASE-INHIBITING ACTIVITY, A PROCESS FOR THEIR PREPARATION AND PHARMACEUTICAL COMPOSITIONS IN WHICH THESE COMPOUNDS ARE PRESENT

The present invention relates to a novel family of chemical compounds possessing a pharmacological activity, in particular a collagenase-inhibiting activity, a process for the production of these compounds and pharmaceutical compositions in which they are present.

Several types of mammal cells secrete metalloproteases which are capable of degrading interstitial collagen. These collagenases (EC 3.4.23.7) are thought to be involved in the pathological course of several important diseases which are characterized by collagen degradation, such as arthritis and arthrosis, periodontal disease, corneal ulceration, epidermolysis bullosa dystrophica, tumoral invasion and bone resorption.

Because collagenase is the enzyme which initiates the proteolytic attack on the collagen molecules (which are broadly resistant to the other proteases), powerful and specific collagenase inhibitor are useful in the treatment of such diseases.

Collagenase is a metalloprotease which contains zinc and which can be inhibited in a non-specific manner by reagents which chelate zinc, such as ethylenediaminetetraacetic acid (EDTA), O-phenanthroline and various thiols. Some natural inhibitors exist, although these are macromolecules which probably cannot be used directly as drugs.

Specific inhibitors have been designed for other metalloproteases by combining an ability to chelate the zinc atom essential to the enzyme activity, with a structure analogous to that of the enzyme substrate, imparting specificity to the inhibitor. Examples of this type of inhibitor for angiotensin converting enzyme (ACE) and enkephalinase are described in European Pat. Nos. 0 012 401 and 0 054 862 respectively, as well as in European Pat. No. 0 082 088, which describes peptide derivatives of the general formula:

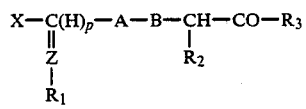

in which, in particular, X represents a radical —CH$_2$CONHOH, the radical >C(H)$_p$=ZR$_1$ can represent a group >CH—CH$_2$—C$_6$H$_5$, the radicals —A—B— can represent a group —CONH—, R$_2$ is a hydrogen atom or an alkyl radical and R$_3$ is a hydroxyl radical or an ester or amide residue.

The present invention relates to inhibitors derived from considerations of the substrate specificity of mammalian collagenase. These inhibitors are powerful and selective and do not inhibit ACE or enkephalinase to a significant degree.

It has in fact been found that a very particular class of hydroxamic acid derivatives, defined by the general formula:

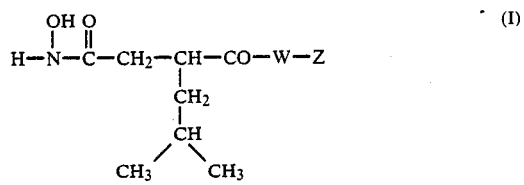

in which:
W represents an amino acid residue selected from the group comprising valine, lysine, norleucine or methionine, and Z represents an amino radical or an alkylamino radical of which the alkyl part, which contains 1 or 2 carbon atoms, is substituted by a phenyl or trifluoromethylphenyl radical, has a collagenase-inhibiting activity and is useful particularly for the treatment of diseases which involve excessive destruction of collagen by collagenase.

The present invention also relates to the diastereoisomers of the compounds of formula (I) and the addition salts of these compounds with pharmaceutically acceptable, non-toxic acids.

More particularly, the present invention relates to compounds of formula I in which: W represents an L-valyl group and Z represents an alkylamino radical of which the alkyl part, which contains 1 or 2 carbon atoms, is substituted by a phenyl or trifluoromethylphenyl radical.

The following compounds are the most representative:

Nα-(N-hydroxy-2-isobutylsuccinamoyl)-L-valinamide:

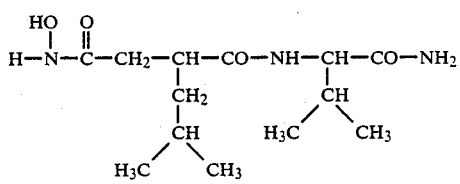

N-benzyl-Nα-(N-hydroxy-2-isobutylsuccinamoyl)-L-valinamide:

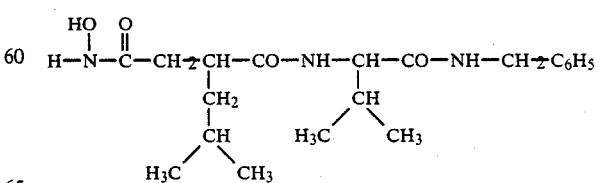

N-(4-trifluoromethylbenzyl)-Nα-(N-hydroxy-2-isobutylsuccinamoyl)-L-valinamide:

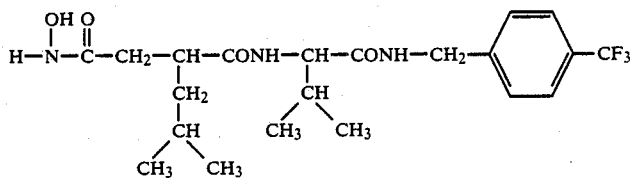

N-phenethyl-Nα-(N-hydroxy-2-isobutylsuccinamoyl)-L-valinamide:

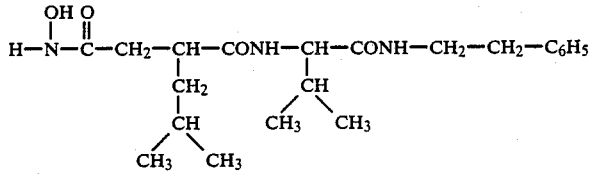

N-benzyl-Nα-(N-hydroxy-2-isobutylsuccinamoyl)-L-norleucine:

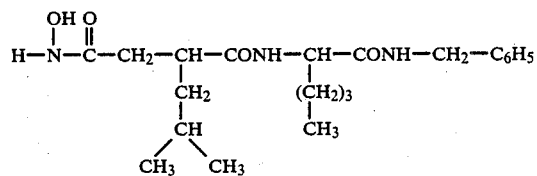

N-benzyl-Nα-(N-hydroxy-2-isobutylsuccinamoyl)-L-lysinamide:

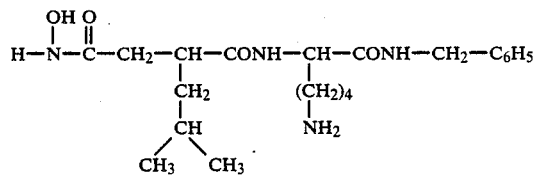

N-benzyl-Nα-(N-hydroxy-2-isobutylsuccinamoyl)-L-methioninamide:

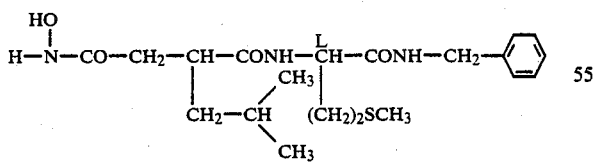

The present invention also relates to pharmaceutical compositions, in particular with collagenase-inhibiting activity, which contain at least one of the compounds defined above as the active ingredient, in association with a pharmaceutically acceptable, non-toxic vehicle or excipient.

The general process for the preparation of the compounds according to the present invention, of the formula:

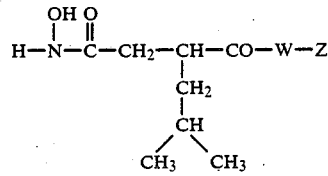

(I)

in which W and Z are defined as above, comprises the following steps:

(1)
(a) the condensation reaction of an acid ester of the formula:

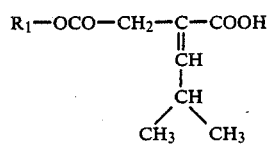

in which $R_1$ denotes an alkyl radical of 1 to 6 atoms, with an amino acid derivative of the formula:

in which W and Z are defined as above, to form the compound of the formula:

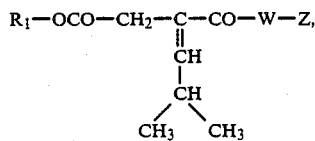

(b) the hydrolysis of the ester formed, in an alkaline medium, to give the corresponding acid, and
(c) the condensation of the resulting acid with O-benzylhydroxylamine to form the derivative:

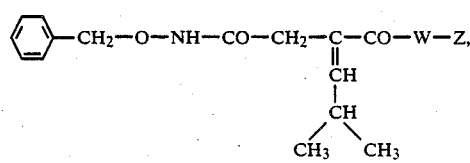

or alternatively:
(a') the condensation reaction of an anhydride of the formula:

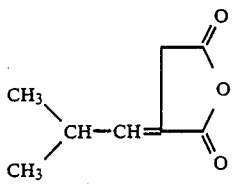

with O-benzylhydroxylamine to form the derivative:

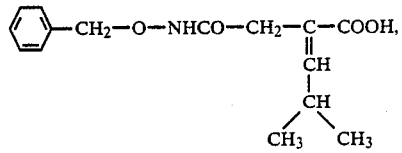

and
(b') the condensation of the resulting acid with an amino acid derivative of the general formula:

H—W—Z in which W and Z are defined as above, to form the derivative:

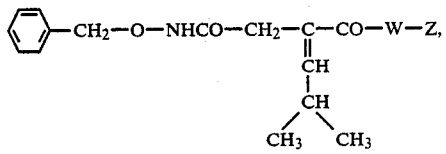

followed by:
(2) the catalytic hydrogenation of the resulting product to give the desired compound according to the present invention,
or, alternatively
(1') the condensation reaction of an anhydride of the formula:

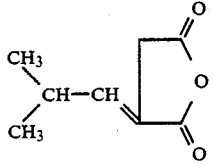

with O-tert.-butoxyhydroxylamine to form 3-N-tert.-butoxycarbamoyl-2-isobutylidenpropanoic acid of the formula

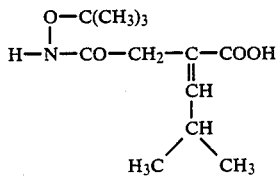

(2') the catalytic hydrogenation of the said acid to form 3-N-tert.-butoxycarbamoyl-2-isobutylpropanoic acid of the formula

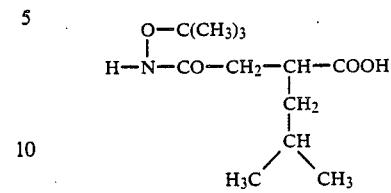

(3') the condensation of the acid thus obtained in (2') with an amino acid derivative of the general formula:

H—W—Z in which W and Z are defined as above, to form the derivative

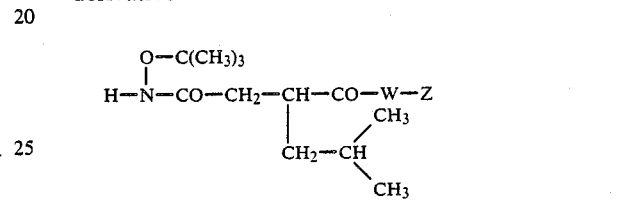

(4') the reaction of the compound thus formed in (3') with a mixture of trifluoracetic acid and boron trifluoracetate to give the desired compound of formula I.

These compounds are obtained in the form of a mixture of diastereoisomers which can be separated by conventional chromatography techniques or by fractional crystallizations.

The starting acid esters used in step (a), and more particularly 3-ethoxycarbonyl-2-isobutylidenepropanoic acid, are valuable intermediates for the synthesis of the compounds of formula (I).

3-Ethoxycarbonyl-2-isobutylidenepropanoic acid can be prepared by a four-step process:
(a) the first step is a condensation reaction of diethyl succinate with isobutyraldehyde;
(b) the second step is an alkaline hydrolysis reaction of the condensation product obtained in the first step to form isobutylidenesuccinic acid; the first step actually gives a complex mixture which is not easy to purify; this mixture is therefore converted in the second step to isobutylidenesuccinic acid, which is purified by fractional crystallizations or precipitations;
(c) in the third step, the resulting diacid undergoes intramolecular dehydration to give a cyclic anhydride; and
(d) in the fourth step, the anhydride undergoes ring opening with selective esterification to give the desired product.

In the following examples, which are given without implying a limitation, the B form is the isomeric form, which has proved to be the more active, as collagenase inhibitor, after separation. In the case where W, in the formula (I) represents a valine residue, the more active isomeric form is characterized in NMR by the chemical shift situated at or below 2 ppm and corresponding to the >CHβ— of the valine; of course the A form is the isomeric form characterized in NMR by the chemical shift situated above 2 ppm and corresponding to the >CHβ— of the valine.

EXAMPLE 1

Nα-(N-Hydroxy-2-isobutylsuccinamoyl)-L-valine (1) Monoethyl isobutylidenesuccinates: $HOOC-CH_2-C[=CH-CH(CH_3)_2]-COOC_2H_5$ and $H_5C_2OOC-CH_2-C[=CH-CH(CH_3)_2]-COOH$ A solution of 10.25 g (142.4 mmol) of isobutyraldehyde and 31 g (178 mmol) of freshly distilled diethyl succinate is added, over a period of 10 min, to 6.1 g (157 mmol) of potassium dissolved in 135 ml of tert.-butanol, heated to the reflux temperature. After refluxing for 5 min, the mixture is cooled and 21 ml of concentrated HCl in 21 g of crushed ice are added. The mixture is evaporated and the resulting residue is triturated in ether. The precipitate is discarded and the ether phase is dried over sodium sulfate, filtered and evaporated to dryness to give an oily product (34.5 g; 97%), Rf=0.61 (silica gel, chloroform/methanol/acetic acid 9/1/0.5), which consists of a mixture of monoethyl isobutylidenesuccinates.

(2) Isobutylidenesuccinic acid, E form: $HOOC-CH_2-C[=CH-CH(CH_3)_2]-COOH$ 34.4 g (172 mmol) of the above monoesters (1) are dissolved in 100 ml of an ethanol-water mixture (2/1). 344 ml of 2.5N sodium hydroxide solution are added to the solution, cooled to 0° C. After stirring for 1 h at 0° C. and then overnight at +4° C. and for 2 h at room temperature, the solution is filtered and then evaporated to dryness. The residue is taken up with water, washed with ethyl acetate (4 times), acidified to pH 2-1 with 3N HCl and extracted with ethyl acetate. The organic solution is then washed with water, dried over sodium sulfate, filtered and then evaporated to dryness to give a white powder (17.4 g; 59%); recrystallization of this compound from water gives the pure diacid in the E form.

Rf=0.39 (chloroform/methanol/acetic acid 9/1/0.5).

Melting point: 200° C.

(3) Isobutylidenesuccinic anhydride 8.2 g (47.9 mmol) of the diacid (2) are dissolved in 144 ml of acetic anhydride. The solution is refluxed for 1 h. After cooling, a precipitate is removed. The solution is evaporated to dryness to give a brown residue containing isobutylidenesuccinic anhydride, which is used as such (7.4 g; 100%).

(4) 3-Ethoxycarbonyl-2-isobutylidenepropanoic acid, E form: $H_5C_2OOC-CH_2-C[=CH-CH(CH_3)_2]-COOH$ A solution of 7.5 g (48.7 mmol) of the anhydride (3) in 97 ml of anhydrous ethanol is refluxed for 3 h. After cooling, the solution is evaporated to dryness to give a thick oil (8.9 g; 91%) which, when crystallized from petroleum ether, gives the expected product—3-ethoxycarbonyl-2-isobutylidenepropanoic acid, E form—in the form of white crystals.

Melting point: 83° C.

Rf=0.56 (chloroform/methanol/acetic acid 9/1/0.5).

(5) $H_5C_2OOC-CH_2-C[=CH-CH(CH_3)_2]-CO-L-valinamide$

The following are added successively to a solution of 1 g (5 mmol) of the acid (4) in dimethylformamide (DMF), cooled to 0° C.:

a solution of 777 mg (5 mmol) of L-valinamide hydrochloride and triethylamine (715 μl) in DMF, a solution of 779 mg (5 mmol) of hydroxybenzotriazole in DMF, and a solution of 1.16 g (5.5 mmol) of N,N-dicyclohexylcarbodiimide (DCC) in DMF.

After stirring for one hour at 0° C. and then for about 20 h at room temperature, the precipitate of dicyclohexylurea (DCU) is filtered off and the filtrate is evaporated to dryness. The resulting residue is taken up with ethyl acetate, filtered again, washed successively with $H_2O$ (twice), 10% citric acid (3 times), $H_2O$ (once), 10% NaHCO$_3$ (3 times), $H_2O$ (once) and a saturated solution of NaCl (once) and then dried over sodium sulfate and evaporated to dryness to give the esteramide (5) in the form of a thick oil (1.2 g; 80%).

Rf=0.76 (chloroform/methanol 7/3)

(6) $HOOC-CH_2-C[=CH-CH(CH_3)_2]-CO-L-valinamide$ 4.2 ml of N sodium hydroxide solution are added to a solution of 1.2 g (3.9 mmol) of the ethyl ester (5) in 10 ml of an ethanol/water mixture (2/1), cooled to 0° C. After stirring for 1 h at 0° C. and then for 1 h at room temperature, the mixture is treated under the same conditions as the compound (2) to give the acid (6) in the form of a foam (1 g; 78%).

(7) $C_6H_5-CH_2O-NHCO-CH_2-C[=CH-CH(CH_3)_2]-CO-L-valinamide$

Starting from 749 mg (2.77 mmol) of the above acid (6) and 442 mg (2.77 mmol) of O-benzylhydroxylamine hydrochloride, a foamy product (394 mg; 38%) is obtained after treatment under the conditions described for the preparation of the compound (5) and after chromatography on silica gel (methylene chloride/ethyl acetate).

Rf=0.23 (ethyl acetate).

(8)

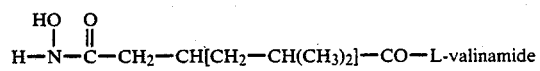

A methanolic solution of 82 mg (0.22 mmol) of the derivative (7) is added to a suspension of 22 mg of 10% palladium-on-charcoal (100 mg/mmol) in 5 ml of methanol and 0.5 ml of acetic acid, saturated with hydrogen beforehand. After stirring for 1 h at room temperature, under a hydrogen atmosphere at ordinary pressure, the catalyst is filtered off and the filtrate is evaporated to dryness in vacuo to give the hydroxamate—Nα-(N-hydroxy-2-isobutylsuccinamoyl)-L-valinamide—in the form of a mixture of diastereoisomers (63 mg; 100%).

Rf=0.57 and 0.63 (chloroform/methanol 7/3).

EXAMPLE 2

N-Benzyl-Nα-(N-hydroxy-2-isobutylsuccinamoyl)-L-valinamide (9) t-Butoxycarbonyl-L-valine benzylamide t-Butoxycarbonyl-L-valine benzylamide (1.4 g; 100%) is obtained by starting from 1 g (4.6 mmol) of t-butoxycarbonyl-L-valine and 493 mg (4.6 mmol) of benzylamine and applying the conditions of treatment described for the preparation of the compound (5).

Rf=0.73 (chloroform/methanol 9/1).

(10) L-Valine benzylamide trifluoroacetate 1.4 g (4.6 mmol) of the above compound (9) are solubilized at 0° C. in 7 ml of trifluoroacetic acid. After stirring for 30 min at 0° C. and then for 30 min at room temperature, the excess acid is evaporated off in vacuo and the residue is washed several times with ether until the pH of the washings is 4, giving a white powder (1.4 g; 96%).

Rf=0.51 (chloroform/methanol 7/3).

(11)  H₅C₂OOC—CH₂—C[=CH—CH(CH₃)₂]—CO—L—valine benzylamide 800 mg (4 mmol) of the acid (4) and 1.28 g (4 mmol) of the trifluoroacetate (10) are treated under the same conditions as for the preparation of the compound (5), giving the ester (11) in the form of a thick oil (1.54 g; 99%).

Rf=0.65 (chloroform/methanol 9/1).

(12)  HOOC—CH₂—C[=CH—CH(CH₃)₂]—CO—L—valine benzylamide 1.47 g (3.78 mmol) of the above ester (11) are treated with 1.62 ml of N sodium hydroxide solution under the same conditions as for the preparation of the compound (2), giving the acid (12) in the form of an oil (902 mg; 66%).

Rf=0.4 (chloroform/methanol/acetic acid 9/1/0.5).

(13)  C₆H₅—CH₂O—NHCO—CH₂—C[=CH—CH(CH₃)₂]—CO—L—valine benzylamide 430 mg (1.2 mmol) of the acid (12) and 190 mg (1.2 mmol) of O-benzylhydroxylamine hydrochloride are treated under the same conditions as for the preparation of the compound (5), giving a foam which, after chromatography on silica gel (methylene chloride/ethyl acetate 8/2), gives the amide (13) (247 mg; 44%).

Rf=0.17 (methylene chloride/ethyl acetate 7/3).

(14)

H—N—C—CH₂—CH[CH₂—CH(CH₃)₂]—CO—L-valine benzylamide 247 mg (0.53 mmol) of the above amide (13) are hydrogenated under the same conditions as for the preparation of the compound (8), giving a mixture of diastereoisomers of the hydroxamate (14) in the form of flakes (143 mg; 72%).

Rf=0.16 and 0.21 (chloroform/methanol 9/1).

Melting point: 145° C.

The two diastereoisomers are then separated on silica gel (chloroform/methanol 9/1) to give the pure isomers (14 A) and (14 B).

NMR 270 MHz (δmobile protons): isomer B: 7.87 ppm (NH-Val); 8.28 ppm (NH-benzylamide); 8.78 ppm (OH); 10.45 ppm (NH-O); isomer A: 8.08 ppm (NH-Val); 8.40 ppm (NH-benzylamide); 8.67 ppm (OH); 10.39 ppm (NH-O).

EXAMPLE 3

N-Benzyl-Nα-(N-hydroxy-2-isobutylsuccinamoyl)-L-valinamide, B form

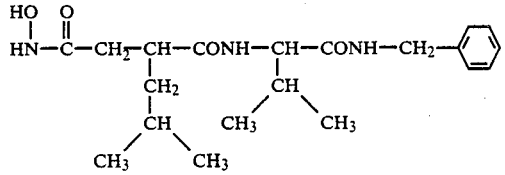

(9) N-Benzyl-Nα-tert.-butoxycarbonyl-L-valinamide

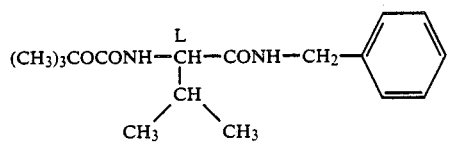

A solution of 150 g (0.73 mol) of dicyclohexylcarbodiimide in 0.5 l of dimethylformamide is added to a solution, stirred at 0° C., of 150 g (0.69 mol) of N-tert.-butoxycarbonyl-L-valine, 74 g (0.69 mol) of benzylamine and 105.8 g (0.69 mol) of hydroxybenzotriazole hydrate in a mixture of 4.5 liters of tetrahydrofuran and 0.5 l of dimethylformamide.

The reaction mixture is stirred for 1 h in the cold and then for 20 h at about 20° C. The dicyclohexylurea in suspension is then filtered off.

The filtrate is concentrated to dryness under reduced pressure (20 mm of mercury, then 0.5 mm of mercury) at 50° C. The residue is taken up with 3 l of ethyl acetate and the suspension is filtered. The filtrate is washed successively:

once with 0.6 l of a 4% w/v aqueous solution of citric acid, twice with a total of 1.2 l of a 4% w/v aqueous solution of sodium bicarbonate, and 5 times with a total of 2 l of an aqueous solution of sodium chloride containing 250 g/l.

The organic phase is dried over sodium sulfate and concentrated to dryness under reduced pressure (20 mm of mercury) at 50° C. to give 213 g (0.69 mol) of the compound (9)—N-benzyl-Nα-tert.-butoxycarbonyl-L-valinamide—in the form of a white solid.

Rf=0.57: silica gel; chloroform/methanol (98/2 by volume).

(10) N-Benzyl-L-valinamide

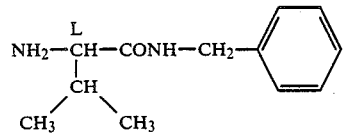

214 g (0.7 mol) of the above compound (9) are solubilized at 0° C. in 650 cm³ of trifluoroacetic acid.

After stirring for 30 min at 0° C. and then for 30 min at 20° C., the solution is concentrated to dryness under reduced pressure (1 mm of mercury) at 35° C.

The resulting oily residue of low fluidity is taken up with 300 cm³ of hexane and concentrated to dryness again (20 mm of mercury, then 1 mm of mercury) at 35° C.

The residue is dissolved in 2.5 l of ethyl acetate to give a solution which is washed successively:

twice with a total of 2.6 l of an aqueous solution of sodium carbonate (8% w/v), once with 0.5 l of distilled water, and 3 times with a total of 1.2 l of an aqueous solution of sodium chloride (250 g/l).

The ethyl acetate phase is dried over sodium sulfate and concentrated to dryness under reduced pressure (20 mm of mercury, then 1 mm of mercury) at 45° C. to give 183 g of N-benzyl-L-valinamide (still partially salified) in the form of a gummy oil, which is used as such in the next synthesis step.

(11) N-Benzyl-Nα-(3-ethoxycarbonyl-2-isobutylidenepropanoyl)-L-valinamide

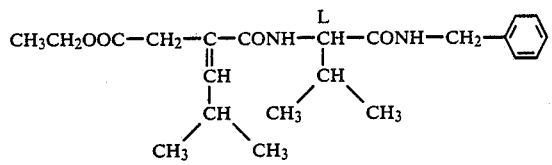

The following are added successively to a solution of 139 g (0.7 mol) of 3-carbethoxy-2-isobutylidenepropanoic acid in 4 l of tetrahydrofuran:
a solution of 184 g (0.7 mol in theory) of the compound (10) in 2 l of tetrahydrofuran,
97 cm³ of triethylamine (0.7 mol), and
107 g (0.7 mol) of hydroxybenzotriazole hydrate.

The stirred mixture is cooled to about 0° C. and a solution of 151 g (0.73 mol) of dicyclohexylcarbodiimide in 1.1 l of chloroform is then added.

After stirring for 1 h at 0° C. and then for 20 h at a temperature of about 20° C., the precipitate of dicyclohexylurea is filtered off and the filtrate is concentrated to dryness under reduced pressure (20 mm of mercury) at 45° C.

The residue is taken up with 1.5 l of ethyl acetate and then filtered to remove the precipitate of dicyclohexylurea.

The filtrate is washed successively:
3 times with a total of 2.1 l of an aqueous solution of sodium bicarbonate (8% w/v),
twice with a total of 1 l of an aqueous solution of citric acid (4% w/v),
once with a mixture of 20 cm³ of an aqueous solution of sodium bicarbonate (10% w/v) and 200 cm³ of an aqueous solution of sodium chloride (250 g/l), and
4 times with a total of 1.6 l of an aqueous solution of sodium chloride (250 g/l).

The ethyl acetate phase is dried over sodium sulfate and then concentrated to dryness under reduced pressure (20 mm of mercury) at 5° C. to give a solid which, after stirring in 10 l of petroleum ether for 5 h, filtration and drying in air, gives 179 g (0.46 mol) of the compound (11)—N-benzyl-Nα-(3-ethoxycarbonyl-2-isobutylidenepropanoyl)-L-valinamide—in the form of a whitish solid.

Rf=0.56: silica gel; ethyl acetate/cyclohexane (1/1 by volume).

Melting point (Kofler): 110° C.
Yield: 66%.

12) N-Benzyl-Nα-(3-carboxy-2-isobutylidenepropanoyl)-L-valinamide

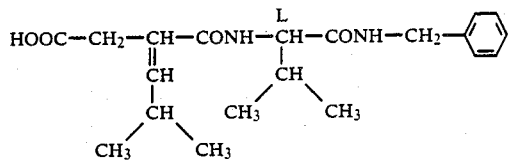

98 cm³ of 1N sodium hydroxide solution are added dropwise, over a period of 30 min, to a stirred solution, cooled to a temperature of about 0° C., of 34.7 g (89 mmol) of the above compound (11) in 140 cm³ of ethanol.

After stirring for 1 h at 0° C. and then for 2 h at a temperature of about 20° C., the reaction mixture is neutralized at 0° C. with 1N hydrochloric acid. The ethanol is driven off by evaporation under reduced pressure (20 mm of mercury) at 50° C.

The aqueous residue is acidified to pH 2 with 1N hydrochloric acid and extracted twice with a total of 1 l of ethyl acetate.

The organic phase is washed successively:
once with 200 cm³ of distilled water, and
3 times with a total of 900 cm³ of an aqueous solution of sodium chloride (250 g/l), and then dried over sodium sulfate and concentrated to dryness under reduced pressure (20 mm of mercury) at 45° C. to give 30 g (83 mmol) of the compound (12) in the form of a whitish meringue.

Rf=0.22: silica gel; chloroform/methanol (96/4 by volume).

Yield: 93%.

(13) N-Benzyl-Nα-(3-N-benzyloxycarbamoyl-2-isobutylidenepropanoyl)-L-valinamide

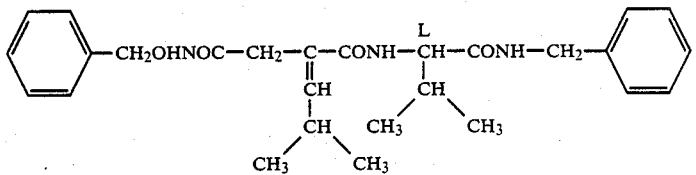

The following are added successively, with stirring, to a solution of 15.7 g (43.6 mmol) of the above compound (12) in 100 cm³ of dimethylformamide at 0° C.:
a solution of 6.95 g (43.6 mmol) of O-benzylhydroxylamine hydrochloride in 150 cm³ of dimethylformamide,
6.1 cm³ (43.6 mmol) of triethylamine,
a solution of 6.68 g (43.6 mmol) of hydroxybenzotriazole hydrate in 100 cm³ of dimethylformamide, and
a solution of 18.5 g (43.6 mmol) of 3-[2-(4-methylmorpholino)ethyl]-1-cyclohexylcarbodiimide p-toluenesulfonate in 100 cm³ of dimethylformamide.

After 1 h at 0° C. and then 20 h at a temperature of about 20° C., the reaction mixture is concentrated to dryness under reduced pressure (1 mm of mercury) at 45° C.

The residue is dissolved in 1 l of chloroform and washed successively:
once with 200 cm³ of distilled water,
once with 400 cm³ of an aqueous solution of sodium bicarbonate (4% w/v),
once with 300 cm³ of an aqueous solution of sodium bicarbonate (0.4% w/v), and
3 times with a total of 600 cm³ of distilled water.

The chloroform phase is dried over sodium sulfate and concentrated to dryness under reduced pressure (20 mm of mercury) at 45° C.

The oil obtained is stirred for 20 h in 300 cm³ of ether to give a white powder which is filtered off and dried in air.

This gives 7.3 g (15.7 mmol) of the compound (13)—N-benzyl-Nα-(3-N-benzyloxycarbamoyl-2-isobutylidenepropanoyl)-L-valinamide—in the form of a white solid.

Rf=0.51: silica gel; chloroform/methanol (90/10 by volume).

Melting point (Kofler): 159° C.

Yield: 36%.

(14) N-Benzyl-Nα-(N-hydroxy-2-isobutylsuccinamoyl)-L-valinamide, B form

A solution of 6.7 g (14.4 mmol) of the compound (13) in 500 cm³ of methanol is added to a suspension of 6.7 g of palladium-on-charcoal (containing 10% of palladium) in 2.7 l of acetic acid and 500 cm³ of methanol, saturated with hydrogen beforehand.

After stirring for 4 h under a hydrogen atmosphere at ordinary temperature, the reaction suspension is purged for 30 min with a stream of nitrogen.

The catalyst is filtered off and the filtrate is concentrated to dryness under reduced pressure (20 mm of mercury, then 1 mm of mercury) at 45° C.

The residue is triturated in 200 cm³ of ether to give a powder which is filtered off and then solubilized in 50 cm³ of a chloroform/methanol mixture (95/5 by volume).

The resulting solution is loaded onto a column of diameter 6.7 cm, containing 1200 g of neutral silica (0.04–0.063 mm), and then eluted with 12 l of a chloroform/methanol mixture (95/5 by volume), 100 cm³ fractions being collected.

Fractions 95 to 120 are combined and concentrated to dryness under reduced pressure (20 mm of mercury) at 45° C. to give 0.46 g (1.22 mmol) of the compound (14)—N-benzyl-Nα-(N-hydroxy-2-isobutylsuccinamoyl)-L-valinamide, B form—in the form of a light beige solid.

Rf=0.38: silica gel; chloroform/methanol (85/15 by volume).

Melting point: 192° C.

NMR DMSO-d₆ (400 MHz, δ in ppm, J in Hz): 10.35, bs, 1H, OH or NH; 8.7, s, 1H, NH or OH; 8.3, t, 1H, NHCH₂; 7.9, d, 1H, NH—CH; 7.20 to 7.30, m, 5H, C₆H₅; 4.20, ABX, 2H, CH₂NH; 4.10, dd, (J=8 and 8), 1H, CHα; 2.75, bm, 1H, CHCO; 2 and 2.15, ABX, 2H, CH₂CO; 2, m, 1H, isopropyl CH; 1.45, m, 1H, isopropyl CH; 1.1 and 1.45, ABXX', 2H, CH₂CH; 0.8, m, 12H, 4×isopropyl CH₃.

EXAMPLE 4

(15) N-(4-Trifluoromethylbenzyl)-Nα-tert.-butoxycarbamoyl-L-valinamide

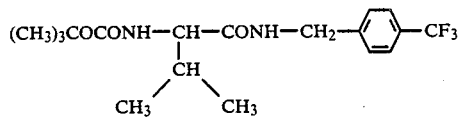

A solution of 4.98 g (24 mmol) of dicyclohexylcarbodiimide in 30 cm³ of chloroform is added to a solution, stirred at +5° C., of 5 g (23 mmol) of N-tert.-butoxycarbonyl-L-valine, 4.02 g (23 mmol) of 4-trifluoromethylbenzylamine and 3.53 g (23 mmol) of hydroxybenzotriazole hydrate in a mixture of 90 cm³ of tetrahydrofuran and 15 cm³ of dimethylformamide.

The reaction mixture is stirred for 1 h at about +5° C. and then for 20 h at about 20° C. The dicyclohexylurea in suspension is then filtered off.

The filtrate is concentrated to dryness under reduced pressure (20 mm of mercury, then 1 mm of mercury) at 50° C.

This gives an oily residue which is dissolved in 300 cm³ of chloroform.

This solution is washed successively:

twice with a total of 200 cm³ of a 2% w/v aqueous solution of sodium bicarbonate, once with 70 cm³ of distilled water, once with 100 cm³ of a 2% w/v aqueous solution of citric acid, then, without waiting, once with 50 cm³ of a 0.05% w/v aqueous solution of sodium bicarbonate, and finally 3 times with a total of 180 cm³ of distilled water.

The chloroform phase is dried over sodium sulfate and concentrated to dryness under reduced pressure (20 mm of mercury) at 40° C.

200 cm³ of ethyl ether are added to the oily residue. The dicyclohexylurea in suspension is filtered off and the filtrate is concentrated again as before, at 40° C.

The resulting white solid is triturated in 100 cm³ of petroluem ether. The suspension is filtered and the solid is dried in air.

This gives 7.9 g (21 mmol) of the compound (15)—N-(4-trifluoromethylbenzyl)-Nα-tert.-butoxycarbamoyl-L-valinamide—in the form of a white solid.

Rf=0.6: silica gel; chloroform/methanol (95/5 by volume).

Melting point (Kofler): 124°–126° C.

Yield: 92%.

(16) N-(4-Trifluoromethylbenzyl)-L-valinamide trifluoroacetate

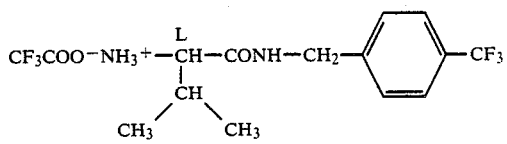

7.9 g (21 mmol) of the above compound (15) are solubilized at 0° C. in a mixture of 40 cm³ of methylene chloride and 25 cm³ of trifluoroacetic acid.

After stirring for 1 h at 0° C., the methylene chloride is driven off under reduced pressure (20 mm of mercury) at 30° C., followed by the excess trifluoroacetic acid (1 mm of mercury) at 30° C.

The resulting oily residue is washed 4 times with a total of 120 cm³ of petroleum ether.

The gummy residue is dissolved in 100 cm³ of ether and then concentrated to dryness under reduced pressure (20 mm of mercury).

After 20 h at a temperature of about 20° C. in a mixture of 200 cm³ of petroleum ether and 30 cm³ of ether, the pasty residue gives a white powder which is filtered off.

The solid is then washed with 20 cm³ of petroleum ether and dried under reduced pressure (20 mm of mercury) at 20° C. to give 7.24 g (18.4 mmol) of the compound (16)—N-(4-trifluoromethylbenzyl)-L-valinamide trifluoroacetate—in the form of a white solid.

Melting point (Kofler): 145°-148° C.

Rf≈0.3: silica gel; chloroform/methanol (80/20 by volume).

Yield: 82%.

(17) N-(4-Trifluoromethylbenzyl)-Nα-(3-ethoxycarbonyl-2-isobutylidenepropanoyl)-L-valinamide Fractions 48 to 74 are combined and concentrated to dryness under reduced pressure (20 mm of mercury) at 50° C. to give 7.15 g (15.6 mmol) of the compound (17)—N-(4-trifluoromethylbenzyl)-Nα-(3-ethoxycarbonyl-2-isobutylidenepropanoyl)-L-valinamide—in the form of white crystals.

Rf=0.3: silica gel; ethyl acetate/cyclohexane (30/70 by volume).

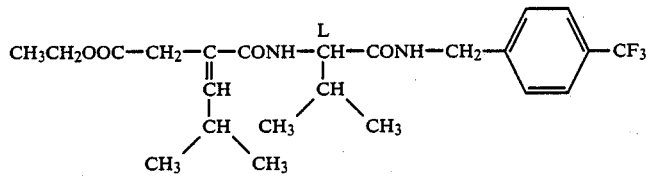

The following are added successively to a solution of 3.69 g (18.4 mmol) of 3-carbethoxy-2-isobutylidene-propanoic acid in 40 cm³ of tetrahydrofuran:

a solution of 7.24 g (18.4 mmol) of the compound (16) and 2.58 cm³ of triethylamine in 70 cm³ of chloroform, and a solution of 2.82 g (18.4 mmol) of hydroxybenzotriazole hydrate in 50 cm³ of tetrahydrofuran.

The stirred mixture is cooled to 0° C. and a solution of 3.98 g (19.3 mmol) of dicyclohexylcarbodiimide in 40 cm³ of chloroform is then added.

After stirring for 1 h at 0° C. and then for about 20 h at a temperature of about 20° C., the precipitate of dicyclohexylurea is filtered off and the filtrate is concentrated to dryness under reduced pressure (20 mm of mercury) at 40° C.

The residue is dissolved in 300 cm³ of chloroform and the solution is washed successively:

twice with a total of 120 cm³ of a 2% w/v aqueous solution of sodium bicarbonate, once with 50 cm³ of distilled water, once with 50 cm³ of a 4% w/v aqueous solution of citric acid, and twice with a total of 100 cm³ of distilled water.

The chloroform phase is dried over sodium sulfate and concentrated to dryness under reduced pressure (20 mm of mercury) at 40° C.

The oily residue is taken up with a mixture of 200 cm³ of ether and 100 cm³ of petroleum ether.

The precipitate of dicyclohexylurea is filtered off. The filtrate is concentrated to dryness under reduced pressure (20 mm of mercury) at 40° C. to give 8.1 g of a yellowish oil which is dissolved in 50 cm³ of an ethyl acetate/cyclohexane mixture (30/70 by volume).

This solution is loaded onto a column of diameter 5 cm, containing 500 g of neutral silica (0.04-0.063 mm), and then eluted successively with:

2.6 l of an ethyl acetate/cyclohexane mixture (30/70 by volume), and 2.0 l of an ethyl acetate/cyclohexane mixture (50/50 by volume), 65 cm³ fractions being collected.

Melting point (Kofler): 98°-100° C.

Yield: 85%.

(18) N-(4-Trifluoromethylbenzyl)-Nα-(3-carboxy-2-isobutylidenepropanoyl)-L-valinamide

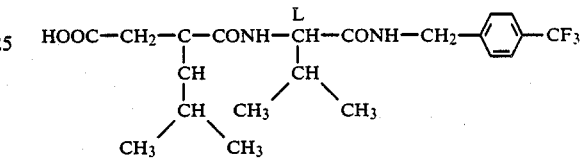

17 cm³ of 1N sodium hydroxide solution are added dropwise, over a period of 15 min, to a stirred solution, cooled to about +5° C., of 7.1 g (15.5 mmol) of the above compound (17) in 35 cm³ of ethanol.

After 30 minutes at about 0° C. and then 2 h at a temperature of about 20° C., the reaction medium is filtered and the filtrate is concentrated to 20 cm³ under reduced pressure (1 mm of mercury) at 20° C.

The oily residue is taken up with 80 cm³ of distilled water and washed twice with a total of 140 cm³ of ether.

The aqueous phase is acidified to pH≈2 with 4N hydrochloric acid and extracted with 300 cm³ of ethyl acetate.

The ethyl acetate phase is washed with 50 cm³ of an aqueous solution of sodium chloride (250 g/l), dried over sodium sulfate and then concentrated to dryness under reduced pressure (20 mm of mercury) at 50° C. to give 5.78 g (13.5 mmol) of the compound (18)—N-(4-trifluoromethylbenzyl)-Nα-(3-carboxy-2-isobutylidenepropanoyl)-L-valinamide—in the form of a white meringue.

Rf=0.25: silica gel; chloroform/methanol (90/10 by volume).

Yield: 87%.

(19) N-(4-Trifluoromethylbenzyl)-Nα-(3-N-benzyloxycarbamoyl-2-isobutylidenepropanoyl)-L-valinamide

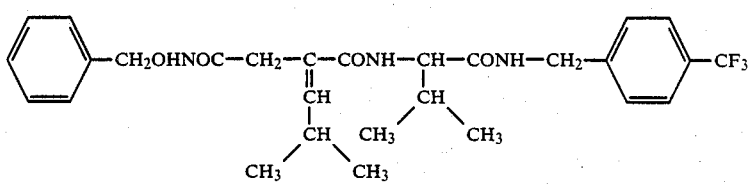

The following are added successively to a solution of 5 g (11.68 mmol) of the compound (18) in 50 cm³ of dimethylformamide:

a solution of 1.86 g (11.68 mmol) of O-benzylhydroxylamine hydrochloride in 100 cm³ of dimethylformamide.

1.63 cm³ (11.68 mmol) of triethylamine, and a solution of 1.79 g (11.68 mmol) of hydroxybenzotriazole hydrate in 50 cm³ of dimethylformamide.

A solution of 4.95 g (11.68 mmol) of 3-[2-(4-methylmorpholino)ethyl]-1-cyclohexylcarbodiimide p-toluenesulfonate in 60 cm³ of dimethylformamide is added to the stirred mixture over a period of 2 min.

After stirring for 24 h at a temperature of about 20° C., the reaction mixture is concentrated to dryness under reduced pressure (1 mm of mercury) at 50° C.

The residue is dissolved in 400 cm³ of chloroform and the solution is washed successively:

twice with a total of 200 cm³ of distilled water, twice with a total of 200 cm³ of an aqueous solution of sodium bicarbonate (4% w/v), twice with a total of 240 cm³ of an aqueous solution of citric acid (4% w/v), and 4 times with a total of 400 cm³ of distilled water.

The chloroform phase is dried over sodium sulfate and concentrated to dryness under reduced pressure (20 mm of mercury) at 50° C.

The resulting white solid is crystallized from 80 cm³ of acetonitrile, filtered off and then dried under reduced pressure (20 mm of mercury) at 20° C.

This gives 2.12 g (3.97 mmol) of the compound (19)—N-(4-trifluoromethylbenzyl)-Nα-(3-N-benzyloxycarbamoyl-2-isobutylidenepropanoyl)-L-valinamide—in the form of a white solid.

Rf = 0.37: silica gel; chloroform/methanol (97/3 by volume).

Melting point (Kofler): 170° C.

Yield: 34%.

(20) N-(4-Trifluoromethylbenzyl)-Nα-(N-hydroxy-2-isobutylsuccinamoyl)-L-valinamide, B form

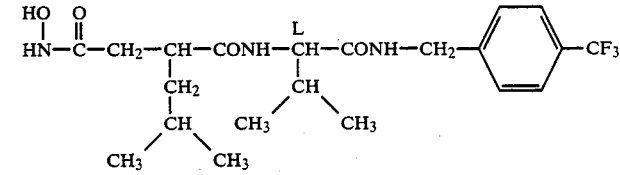

A solution of 2.1 g (3.94 mmol) of the compound (19) in 30 cm³ of methanol and 2.5 cm³ of acetic acid is added to a suspension of 2.1 g of palladium-on-charcoal (containing 10% of palladium) in 30 cm³ of methanol and 2.5 cm³ of acetic acid, saturated with hydrogen beforehand.

After stirring under a hydrogen atmosphere for 4 h at a temperature of about 20° C., the reaction suspension is purged for 30 min with a stream of nitrogen.

The catalyst is filtered off and the filtrate is concentrated to dryness under reduced pressure (20 mm of mercury) at 40° C.

The residue is triturated in 100 cm³ of ether to give a powder which is filtered off and then solubilized in 30 cm³ of methanol.

This solution is treated with 2 g of neutral silica (0.04–0.063 mm) and concentrated to dryness under reduced pressure (20 mm of mercury) at 40° C.

The solid obtained is suspended in 20 cm³ of a chloroform/methanol mixture (90/10 by volume), loaded onto a column of diameter 3.6 cm, containing 150 g of neutral silica (0.04–0.063 mm), and then eluted with 750 cm³ of a chloroform/methanol mixture (90/10 by volume), 15 cm³ fractions being collected.

Fractions 39 to 48 are combined and concentrated to dryness under reduced pressure (20 mm of mercury) at 50° C.

The residue is triturated in 50 cm³ of ether to give a powder which is filtered off and dried under reduced pressure (20 mm of mercury) at 20° C. to give 0.16 g (0.36 mmol) of the compound (20)—N-(4-trifluoromethylbenzyl)-Nα-(N-hydroxy-2-isobutylsuccinamoyl)-L-valinamide, B form.

Rf = 0.29: silica gel; chloroform/methanol (90/10 by volume).

Melting point (Kofler): 228° C. (unsharp).

NMR spectrum (DMSO-d6, 250 MHz, δ in ppm, J in Hz): 10.4, bs, 1H, NH or OH; 8.70, bs, 1H, OH or NH; 8.50, t, 1H, NH—CH2; 7.95, d, (J=8.5), 1H, NHCH; 7.45 and 7.65, AB, (J=8), 4H, C6H4; 4.35, bm, limiting ABX, 2H, CH2N; 4.10, dd, (J=8.5 and 8), 1H, CHX; 2.80, m, 1H, CHCO; 2.15 and 2, ABX, 2H, CH2CO; 2, m, 1H, isopropyl CH; 1.4, m, 1H, isopropyl CH; 1.4 and 1.05, 2m, 2H, CH2; 0.7 to 0.9, 4d, 4×3H, 4 Me.

EXAMPLE 5

(21) N-Phenethyl-Nα-tert.-butoxycarbonyl-L-valinamide

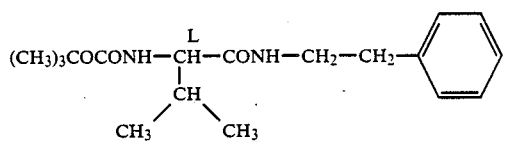

7.3 g (22.8 mmol) of the compound (21)—N-phenethyl-Nα-tert.-butoxycarbonyl-L-valinamide—are obtained in the form of a white solid by starting from 5 g (23 mmol) of N-tert.-butoxycarbonyl-L-valine and 2.7 g (23 mmol) of 2-phenylethylamine and applying the conditions of treatment described in the preparation of the compound (15).

Rf = 0.6: silica gel; chloroform/methanol (95/5 by volume).

Melting point (Kofler): 119° C.

Yield ≈ 100%.

(22) N-Phenethyl-L-valinamide trifluoroacetate

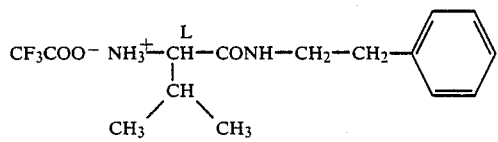

7.3 g (22.8 mmol) of the above compound (21) are dissolved at 0° C. in a mixture of 40 cm³ of methylene chloride and 2.5 cm³ of trifluoroacetic acid.

After stirring for 30 min at 0° C. and then for 1 h at a temperature of about 20° C., the methylene chloride is driven off under reduced pressure (20 mm of mercury) at 30° C., followed by the excess trifluoroacetic acid (1 mm of mercury) at 30° C.

The oily residue is washed 5 times with a total of 1.5 l of petroleum ether to give a white suspension.

The solid is filtered off, then recrystallized from 150 cm³ of ether and then dried under reduced pressure (20 mm of mercury) at 20° C.

This gives 6.0 g (18 mmol) of the compound (22)—N-phenethyl-L-valinamide trifluoroacetate—in the form of white crystals.

Rf=0.40: silica gel; chloroform/methanol (80/20 by volume).

Melting point (Kofler): 124° C.
Yield: 80%.

(23) N-Phenethyl-Nα-(3-ethoxycarbonyl-2-isobutylidenepropanoyl)-L-valinamide isobutylidenepropanoyl)-L-valinamide—in the form of a white meringue.

Rf=0.35: silica gel; chloroform/methanol (90/10 by volume).

Yield: 82%.

(25) N-Phenethyl-Nα-(3-N-benzyloxycarbamoyl-2-isobutylidenepropanoyl)-L-valinamide

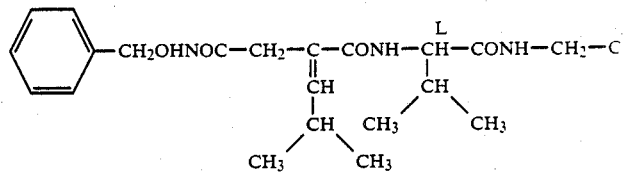

The following are added successively, with stirring, to a solution of 3.0 g (8.1 mmol) of the compound (24) in 70 cm³ of dimethylformamide:

a solution of 1.29 g (8.1 mmol) of O-benzylhydroxylamine hydrochloride in 50 cm³ of dimethylformamide,
1.13 cm³ (8.1 mmol) of triethylamine, and

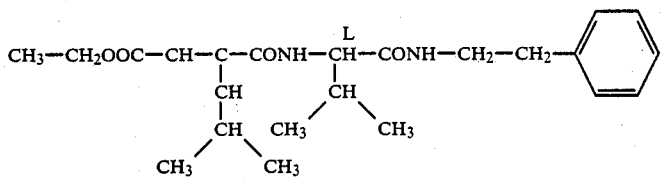

By starting from 4 g (11.9 mmol) of the above compound (22) and 2.39 g (11.9 mmol) of 3-carbethoxy-2-isobutylidenepropanoic acid and applying the conditions of treatment described in the preparation of the compound (17), a crude solid product is obtained which, after washing with a solution of 100 cm³ of ether and 50 cm³ of petroleum ether, gives 4.77 g (11.9 mmol) of the compound (23)—N-phenethyl-Nα-(3-ethoxycarbonyl-2-isobutylidenepropanoyl)-L-valinamide—in the form of a whitish gel.

Rf=0.48: silica gel; ethyl acetate/cyclohexane (50/50 by volume).

Yield: 100%.

(24) N-Phenethyl-Nα-(3-carboxy-2-isobutylidenepropanoyl)-L-valinamide 1.24 g (8.1 mmol) of hydroxybenzotriazole hydrate.

A solution of 3.46 g (8.16 mmol) of 3-[2-(4-methylmorpholino)ethyl]-1-cyclohexylcarbodiimide p-toluenesulfonate in 30 cm³ of dimethylformamide is added to the mixture, cooled to 10° C., over a period of 2 min.

After stirring for 1 h at 10° C. and then for 24 h at a temperature of about 20° C., the reaction mixture is concentrated to dryness under reduced pressure (1 mm of mercury) at 50° C.

The residue is dissolved in 300 cm³ of chloroform.

The resulting solution is washed under the conditions described for the preparation of the compound (19) and the concentrated to dryness under reduced pressure (20 mm of mercury) at 50° C.

The resulting solid is triturated in 50 cm³ of ether,

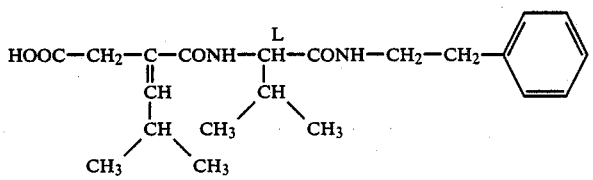

13 cm³ of 1N sodium hydroxide solution are introduced slowly, with stirring, into a solution of 4.75 g (11.8 mmol) of the compound (23) in 40 cm³ of ethanol, cooled to about 10° C.

After stirring for 30 min at 10° C. and for 2 h at a temperature of about 20° C., the reaction solution is treated under the same conditions as for the preparation of the derivative (18) to give 3.63 g (9.7 mmol) of the compound (24)—N-phenethyl-Nα-(3-carboxy-2- filtered off and then crystallized from 40 cm³ of acetonitrile to give 1.1 g (2.29 mmol) of the compound (25)—N-phenethyl-Nα-(3-N-benzyloxycarbamoyl-2-isobutylidenepropanoyl)-L-valinamide—in the form of a white solid.

Rf=0.8: silica gel; chloroform/methanol (90/10 by volume)

Melting point (Kofler): 182° C.
Yield: 28%.

(26) N-Phenethyl-Nα-(N-hydroxy-2-isobutylsuccinamoyl)-L-valinamide, B form

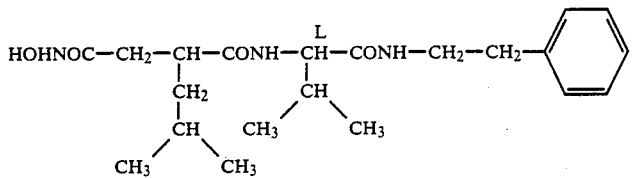

A solution of 1.1 g (2.29 mmol) of the compound (25) in 45 cm³ of methanol and 2 cm³ of acetic acid is added to a suspension of 1.1 g of palladium-on-charcoal (containing 10% of palladium) in 15 cm³ of methanol and 3 cm³ of acetic acid, saturated with hydrogen beforehand.

After stirring for 4 h at ordinary pressure, the reaction suspension is purged for 30 min with a stream of nitrogen.

The catalyst is filtered off and the filtrate is concentrated to dryness under reduced pressure (20 mm of mercury, then 1 mm of mercury) at 40° C.

The residue is triturated in 100 cm³ of ether to give a powder which is filtered off and then solubilized in 20 cm³ of a chloroform/methanol mixture (96/4 by volume).

The solution is loaded onto a column of diameter 3.4 cm, containing 200 g of neutral silica (0.04–0.063 mm), and then eluted with 2.5 l of a chloroform/methanol mixture (96/4 by volume), 20 cm³ fractions being collected.

Fractions 107 to 125 are combined and concentrated to dryness under reduced pressure (20 mm of mercury) at 50° C.

The residue is triturated in ether, filtered off and dried under reduced pressure (20 mm of mercury) at 20° C. to give 57 mg (0.15 mmol) of the compound (26)—N-phenethyl-Nα-(N-hydroxy-2-isobutylsuccinamoyl)-L-valinamide, B form—in the form of a light beige solid.

Rf=0.38: silica gel; chloroform/methanol (90/10 by volume).

Melting point (Kofler): 192° C.

NMR spectrum, DMSO-d₆ (250 MHz, δ in ppm, J in Hz): 10.4, bs, 1H, NH or OH; 8.7, bs, 1H, NH or OH; 7.95, t, 1H, NHCH₂; 7.80, d, (J=8.5), 1H, NHCH; 7.15 to 7.35, m, 5H, C₆H₅; 4.10, dd, (J=8.5 and 8.5), 1H, CHα; 3.30, m, 2H, CH₂NH; 2.80, m, 1H, CHCO; 2.70, t, 2H, CH₂—C₆H₅; 2 and 2.15, ABX, 2H, CH₂CO; 1.9, m, 1H, isopropyl CH; 1.45, m, 1H, isopropyl CH; 1.05 and 1.45, m, 2H, CH₂; 0.80, m, 4×3H, 4 CH₃.

EXAMPLE 6

N-Benzyl-Nα-(N-hydroxy-2-isobutylsuccinamoyl)-L-norleucinamide

(27) 3-N-Benzyloxycarbamoyl-2-isobutylidene-propanoic acid

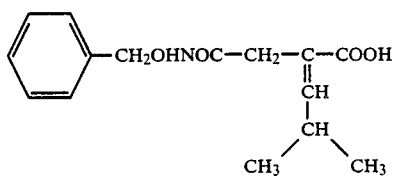

A solution of O-benzylhydroxylamine hydrochloride (1.41 g; 8.86 mmol) in 10 cm³ of dry toluene and 1.24 cm³ of triethylamine (8.86 mmol) is added to a solution of 1.1 g (7.38 mmol) of isobutylidenesuccinic anhydride in 8 cm³ of dry toluene. After stirring for 10 min, the precipitate formed is filtered off and the organic phase is extracted with water and N sodium hydroxide solution. The combined alkaline aqueous solutions (pH 9) are acidified to pH 2-1 with N HCl and then extracted with ether (2×25 cm³). The combined ether phases are washed with water (25 cm³), dried over sodium sulfate crystals, filtered and then concentrated to dryness under reduced pressure to give the expected product in the form of an oil (1.22 g; 60%).

Rf=0.54 (chloroform/methanol/acetic acid 9/1/0.1).

(28) N-Benzyl-Nα-tert.-butoxycarbonyl-L-norleucinamide

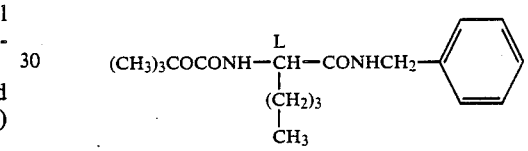

3.8 g (16.43 mmol) of tert.-butoxycarbonylnorleucine in 15 cm³ of dimethylformamide (DMF) and 1.76 g (16.43 mmol) of benzylamine are condensed in the presence of 2.52 g (16.43 mmol) of hydroxybenzotriazole in 15 cm³ of DMF and 3.73 g (18.07 mmol) of dicyclohexylcarbodiimide in 15 cm³ of DMF. A thick oil (5.45 g; 104%) is obtained after treatment under the same conditions as for the preparation of the compound (5). This oil is treated by flash chromatography: column diameter=5 cm; height of silica=15 cm; eluent=ether/cyclohexane 5/5; fractions collected=60 cm³. Fractions 7 to 17 are combined and concentrated to dryness under reduced pressure to give the expected compound in the form of a thick oil (5.09 g; 97%).

Rf=0.33 (ether/cyclohexane 5/5).

(29) N-Benzyl-L-norleucinamide

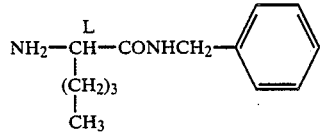

5.08 g (15.85 mmol) of the compound (28) are stirred for 30 min at 0° C. and then for 30 min at room temperature in the presence of 23 cm³ of trifluoroacetic acid (1.5 cm³/mmol). After treatment under the same conditions as for the preparation of the compound (10), the expected product is obtained in the form of a foam (4.23 g; 80%).

Rf=0.2 (chloroform/methanol/acetic acid).

(30) N-Benzyl-Nα-(3-N-benzyloxycarbamoyl-2-isobutylidenepropanoyl)-L-norleucinamide

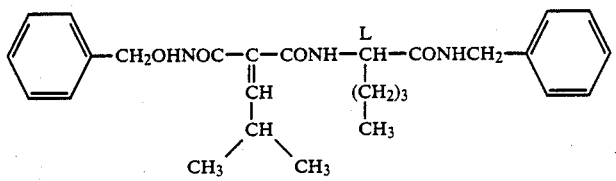

The following are added successively to a solution of 800 mg (2.28 mmol) of the acid (27) in 5 cm³ of dimethylformamide and 0.381 cm³ of triethylamine, cooled to 0° C.:

a solution of 1.09 g (3.25 mmol) of N-benzyl-L-norleucinamide trifluoroacetate in 10 cm³ of dimethylformamide and 0.454 cm³ of triethylamine, and a solution of 612 mg (2.97 mmol) of dicyclohexylcarbodiimide in 5 cm³ of dimethylformamide.

After stirring for 1 h at 0° C. and then for about 20 h at room temperature, the reaction mixture is treated under the same conditions as for the preparation of the compound (5). The resulting residue is precipitated from an ether/petroleum ether mixture (1/1) to give the expected product in the form of a white powder (900 mg; 65%).

Rf=0.31 (chloroform/methanol/acetic acid 9/1/0.1).

(31) N-Benzyl-Nα-(N-hydroxy-2-isobutylsuccinamoyl)-L-norleucinamide

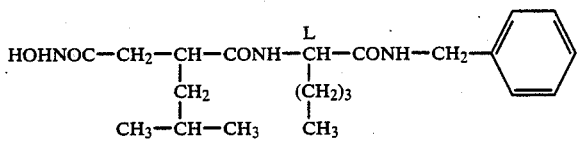

90 mg (0.19 mmol) of the compound (30) are hydrogenated in the presence of 38 mg of 10% palladium-on-charcoal (200 mg/mmol) in 2 cm³ of methanol and 0.100 cm³ of acetic acid. When the reaction has ended, the reaction mixture is treated under the same conditions as for the preparation of the compound (8) to give a pasty solid. This solid is dissolved in 0.209 cm³ of N sodium hydroxide solution (pH 6) and stirred for 1 h. A small amount of insoluble material is then removed and the filtrate is concentrated to dryness under reduced pressure. The resulting residue is taken up with 15 cm³ of water.

The resulting aqueous solution (pH 6) is extracted with 3×10 cm³ of ethyl acetate. The organic phases are combined, dried over sodium sulfate crystals, filtered and concentrated to dryness under reduced pressure to give the expected product (A) in the form of a foam (23 mg; 32%); this product consists of a mixture of 2 diastereoisomers: A+B.

Rf (identical)=0.49 (chloroform/methanol/acetic acid 9/1/0.1).

NMR DMSO-d₆ (270 MHz, δ in ppm): broad peak centred at 10.36 ppm (1H, NHO); broad peak centred at 8.70 (1H, N—OH); 8.36 and 8.25 (1H, t, NH—CH₂C₆H₅); 8.25 and 7.91 (1H, d NH—Nle); 7.18 (5H, m, C₆H₅—); unresolved signal centred at 4.2 (3H, CH₂—C₆H₅+Hα Nle); broad peak centred at 2.66 (1H,

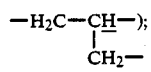

between 2.25 and 1.89 (4H, m,

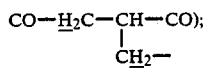

1.73 and 1.58 (1H, unresolved signal,

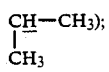

between 1.52 and 0.88 (9H, —(CH₂)₃ and CH₃—CH₂); 0.77 (6H,

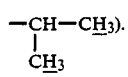

EXAMPLE 7

(32) N-Benzyl-Nα-benzyloxycarbonyl-Nε-tert.-butoxycarbonyl-L-lysinamide

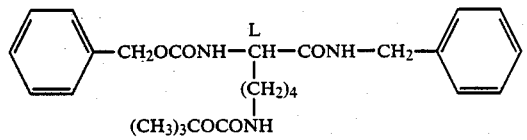

5 g (13.14 mmol) of Nα-benzyloxycarbonyl-Nε-tert.-butoxycarbonyl-L-lysine in 30 cm³ of dry DMF and 1.41 g (13.14 mmol) of benzylamine are condensed in the presence of 2.01 g (13.14 mmol) of hydroxybenzotriazole in 10 cm³ of dry DMF and 2.98 g (14.54 mmol) of dicyclohexylcarbodiimide in 10 cm³ of dry DMF. A pasty solid is obtained after treatment under the same conditions as for the preparation of the compound (5). This solid is covered with ether to give a precipitate of N-benzyl-Nα-benzyloxycarbonyl-Nε-tert.-butoxycarbonyl-L-lysinamide (5.51 g; 89%).

Rf=0.72 (chloroform/methanol 9/1).
Melting point: 105° C.

(33) N-Benzyl-Nε-tert.-butoxycarbonyl-L-lysinamide

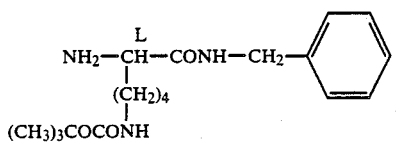

3 g (6.4 mmol) of the above compound (32) are solubilized in 20 cm³ of methanol and added to a suspension of 384 mg of 10% palladium-on-charcoal (100 mg/mmol) in 5 cm³ of methanol, saturated with hydrogen beforehand. After stirring for 4 h at room temperature, under a hydrogen atmosphere at ordinary pressure, the catalyst is filtered off; the filtrate is concentrated to dryness under reduced pressure to give N-benzyl-Nε-tert.-butoxycarbonyl-L-lysinamide in the form of a thick oil (2.15 g; 100%).

Rf=0.37 (chloroform/methanol 9/1).

(34) N-Benzyl-Nα-(3-ethoxycarbonyl-2-isobutylidenepropanoyl)-Nε-tert.-butoxycarbonyl-L-lysinamide

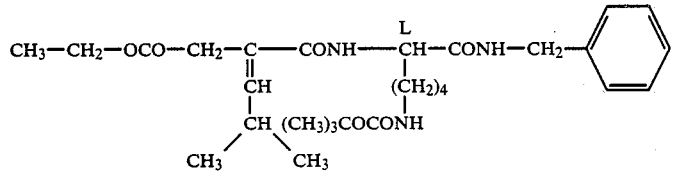

597 mg (2.98 mmol) of 3-ethoxycarbonyl-2-isobutylidenepropanoic acid in 10 cm³ of DMF and 1 g (2.98 mmol) of N-benzyl-Nε-tert.-butoxycarbonyl-L-lysinamide are condensed in the presence of 456 mg (2.98 mmol) of hydroxybenzotrizole in 5 cm³ of DMF and 676 mg (3.28 mmol) of dicyclohexylcarbodiimide in 5 cm³ of DMF. After treatment under the same conditions as for the preparation of the compound (5), the expected product is obtained in the form of a thick oil (1.50 g; 100%).

Rf=0.71 (chloroform/methanol 9/1).

(35) N-Benzyl-Nα-(3-carboxy-2-isobutylidenepropanoyl)-Nε-tert.-butoxycarbonyl-L-lysinamide

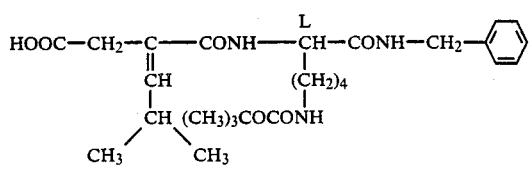

583 mg (1.13 mmol) of the above compound (34) dissolved in 5 cm³ of ethanol/water 3/1 are stirred for 1 h at 0° C. and then for 2 h at room temperature in the presence of ½ cm³ of N sodium hydroxide solution. When the reaction has ended and after treatment under the same conditions as for the preparation of the compound (2), the expected product is obtained in the form of a foam (4.59 mg; 83%).

Rf=0.47 (chloroform/methanol/acetic acid 9/1/0.1).

(36) N-Benzyl-Nα-(3-N-benzyloxycarbamoyl-2-isobutylidenepropanoyl)-Nε-tert.-butoxycarbonyl-L-lysinamide

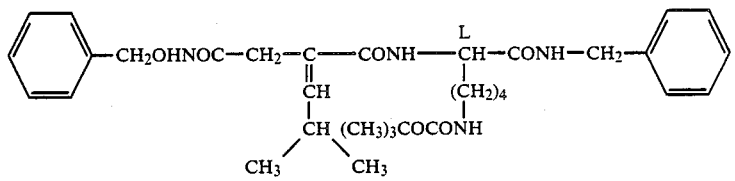

445 mg (0.91 mmol) of the above compound (35) in 10 cm³ of DMF and 145 mg (0.91 mmol) of O-benzylhydroxylamine hydrochloride in 3 cm³ of DMF and 0.128 cm³ of triethylamine are condensed in the presence of 139 mg (0.91 mmol) of hydroxybenzotriazole in 5 cm³ of DMF and 207 mg (1 mmol) of dicyclohexylcarbodiimide in 2 cm³ of DMF. After treatment under the same conditions as for the preparation of the compound (5), the expected product is obtained in the form of a thick oil (447 mg; 83%).

Rf=0.65 (chloroform/methanol 9/1).

(37) N-Benzyl-Nα-(N-hydroxy-2-isobutylsuccinamoyl)-Nε-tert.-butoxycarbonyl-L-lysinamide

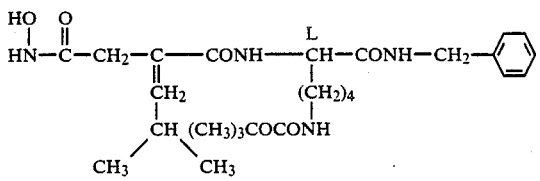

60 mg (0.1 mmol) of the above compound (36) in 1 cm³ of methanol are added to a suspension of 16 mg of 10% palladium-on-charcoal in 2 cm³ of a methanol/acetic acid/water mixture (4/5/1), saturated with hydrogen beforehand. After stirring for 3 h at room temperature under a hydrogen atmosphere, and after treatment under the same conditions as for the preparation of the compound (8), the expected derivative is obtained in the form of a thick oil (51 mg; 100%).

Rf=0.28 (chloroform/methanol 9/1).

(38) N-Benzyl-Nα-(N-hydroxy-2-isobutylsuccinamoyl)-L-lysinamide trifluoroacetate

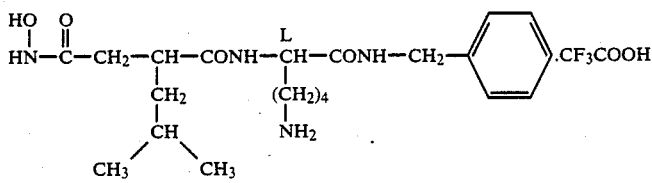

50 mg (0.1 mmol) of the above compound (37) are stirred for 30 min at 0° C. and then for 1 h at room temperature in the presence of 0.150 cm$^3$ of trifluoroacetic acid. After treatment under the same conditions as for the preparation of the compound (10), the expected products are obtained in the form of a foam (41 mg; 79%); this foam consists of 2 diastereoisomers.

Rf (identical)=0.49 (chloroform/methanol 9/1).

NMR DMSO-d$_6$ (270 MHz, δ in ppm): broad peak centred at 10.45 (1H, NH—O); 8.7 (1H, broad, N—OH); 8.37 and 8.13 (1H, t, NH—CH$_2$—C$_6$H$_5$); 8.22 and 7.9 (1H, d, NHα-lys); broad peak centred at 7.62 (3H, NH4); 7.16 (5H, m, C$_6$H$_5$); unresolved signal centred at 4.2 (3H, CH$_2$—C$_6$H$_5$+Hα-lys); 2.65 (2H, broad peak, —CH$_2$—N—lys); between 2.35 and 1.88 (5H,

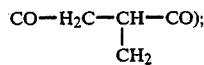

1.73 and 1.58 (1H, m,

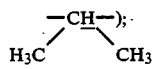

between 1.55 and 0.91 (6H, —CH—(CH$_2$)$_2$—CH$_2$—N—+CH$_2$—ipr); 0.79 (6H, m,

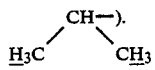

EXAMPLE 8

N-benzyl-N (N-hydroxy-2-isobutylsuccinamoyl)-L-methioninamide

(39) N-benzyl-N-tert.-butoxycarbonyl-L-methioninamide

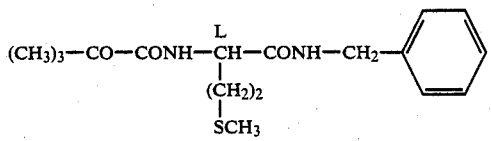

5.01 g (20.1 mmol) of tert.-butoxycarbonyl-L-methionine in 15 cm$^3$ of dimethylformamide (DMF) and 2.15 g (20.1 mmol) of benzylamine are condensed in the presence of 3.08 g (20.1 mmol) of hydroxybenzotriazole in 6 cm$^3$ of DMF and 4.56 g (22.1 mmol) of dicyclohexylcarbodiimide in 10 cm$^3$ of DMF. A solid (6.8 g; 100%); Rf=0.79 (chloroform/methanol 9/1); Melting point=90° C., is obtained after treatment under the same conditions as for the preparation of the compound (5) and after precipitation with ether.

(40) N-benzyl-L-methioninamide

2 g (5.91 mM) of the compound (39) are treated under the same conditions as for the preparation of the compound (29) to give the expected product in the form of white needles (2.07 g, 99%), Rf=0.29 (chloroform/methanol/acetic acid 9/1/0.1).

(41) 3-N-tert.-butoxycarbamoyl-2-isobutylidene-propanoic acid

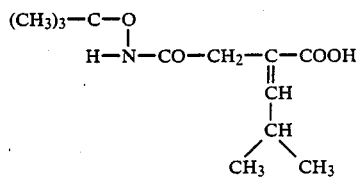

1.1 g (7.38 mmol) of isobutylidenesuccinic anhydride in 8 cm$^3$ of dry toluene; 1.11 g (8.86 mmol) of O-tert.-butylhydroxylamine hydrochloride in 10 cm$^3$ of dry toluene and 1.24 cm$^3$ (8.86 mM) of triethylamine are treated under the same conditions as for the preparation of the compound (27) to give the expected product in the form of a white solid (1.03 g; 57%) Rf=0.21 (chloroform/methanol 9/1).

(42) 3-N-tert.-butoxycarbamoyl-2-isobutylpropanoic acid

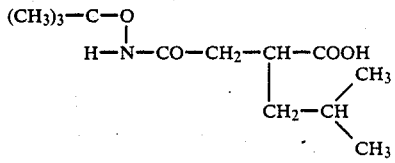

500 mg (2.05 mmol) of the compound (42) dissolved in 5 cm$^3$ of methanol are hydrogenated in the presence of a suspension of 200 mg of 10% palladium-on-charcoal in 5 cm$^3$ of methanol, under the same conditions as for the preparation of the compound (8) to give the expected product in the form of a white crystalline powder (500 mg 99%); Rf=0.26 (chloroform/methanol 9/1); Melting point=157° C.

(43) N-benzyl-N-(3-N-tert.-butoxycarbamoyl-2-isobutylpropanoyl)-L-methioninamide

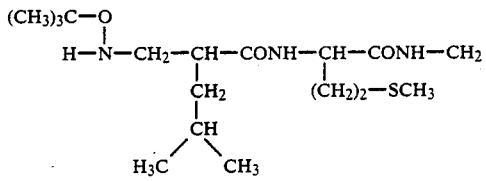

200 mg (0.81 mmol) of the acid (42) in 5 cm³ of chloroform and 0.107 cm³ of triethylamine and 2.19 mg (0.92 mmol) of N-benzyl-L-methioninamide in 10 cm³ of chloroform are condensed in the presence of 172 mg (0.83 mmol) of dicyclohexylcarbodiimide under the same conditions as for the preparation of the compound (30) to give the expected product in the form of a thick oil (322 mg; 85%); Rf=0.58 (chloroform/methanol 9/1).

(44) N-benzyl-N-(N-hydroxy-2-isobutylsuccinamoyl)-L-methioniamide

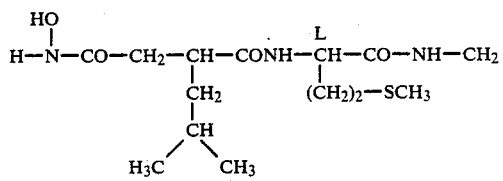

320 mg (0.69 mmol) of the compound (43) are stirred for 30 min at 0° C. in the presence of 2 cm³ of trifluoroacetic acid and 2 cm³ of boron trifluoroacetate. The mixture is then concentrated to dryness under reduced pressure to give a residue which is taken up with ether to give a mixture of diastereoisomers (290 mg). 280 mg of the mixture are treated by flash chromatography (column diameter: 3 cm) and fractions of 20 cm³ are collected with an eluent gradient of chloroform/methanol 9/1 and 7/3 to eliminate impurities in the head of the column. The two diastereoisomers (90 mg/32%) are eluted in the fractions 51 to 55, with a methanol/acetic acid mixture 10/0.25. 50 mg of the product thus eluted are separated onto a column containing silica (column diameter: 1.2 cm; silica height: 60 cm; eluent: chloroform/methanol/acetic acid 10/0.5/0.1; fractions: 350 drops delivery: 1 drop every 4 sec) to give the two-isomers: 22 mg (fractions 28 to 39) and 15 mg (fractions 40 to 75); Rf=0.30 and 0.19 (chloroform/methanol/acetic acid 10/0.5/0.1). This method of preparation is particularly useful when W is a methionine residue since other methods do not give the desired product.

The anticollagenase activity of the compounds according to the present invention was determined on synovial collagenase of porcine or human origin, isolated from synovial cells in culture according to the procedure described by Cawston and Barrett (Cawston and Barrett (1979), Anal. Biochem. 99, 340-345). The collagenase was incubated at 37° C. with radiolabeled collagen and its activity was determined by the release of the soluble peptides produced by enzymatic degradation of the collagen. The inhibitory concentration IC$_{50}$ for each compound was determined by measuring the activity of the enzyme in the presence of the inhibitor at a concentration of between $10^{-5}$ and $10^{-8}$M.

Representative results of these tests are given for the compounds according to the invention in Table I.

Anticollagenase activity has also been determined in a bone resorption model described by Delaissé et al. (Delaissé et al. (1985), Biochem. Biophys. Res. commun., 133, 483-490). This model, which utilizes the degradation of cartilage and bone in an isolated organ, is more physiological than direct determination of the enzyme activity in vitro. The results of the tests are collated in Table II; the same inhibitors are found to be active in both systems.

The specificity of the inhibition was measured by studying several other enzymes, including metalloproteases other than collagenase. The inhibitors according to the invention showed a considerable activity towards collagenase.

The stability of the compounds according to the invention to the influence of proteolytic enzymes was also studied. The most powerful inhibitors were found to be resistant to the following proteases: aminopeptidase M, thermolysine, carboxypeptidase A and B, chymotrypsin, trypsin, thrombin, ACE, papain, pepsin, kallikrein and gastric and intestinal juices.

The toxicity of the compounds was evaluated in vitro on human cells in culture and on animals. No significant cytotoxicity was observed and no toxicity was observed in mice at a dose of 0.5 g/kg, administered subcutaneously.

Thus, the compounds according to the present invention are useful as drugs in the treatment of diseases which involve excessive destruction of collagen by collagenase. As mentioned in the introduction, these diseases include arthritis, arthrosis, periodontal disease, ulcerations, other diseases involving destruction of the connective tissue and, possibly, tumoral invasion and bone resorption.

The mode of administration of the collagenase inhibitors according to the invention depends on the disease to be treated and can be local administration (ulceration, periodontal disease) or systemic administration (enteral or parenteral) for other indications. For example, in the treatment of arthritis, the compound can be administered orally, intravenously, subcutaneously or intramuscularly or, if appropriate, directly into the affected tissues by intraarticular injection. The compounds can be used in aqueous solution, or in the form of an ointment, gel or similar formulation for local applications, or, if appropriate, in a pharmaceutical form which permits a slow release of the product, for example through encapsulation in an inert polymer.

The dose of the compound depends on the mode of administration, the formulation selected and the condition of the subject being treated, and can be between 100 µg and 10 mg/kg as a single or repeat dose.

TABLE I

| ANTICOLLAGEN ACTIVITY | | |
|---|---|---|
| Compound | % inhibition | Concentration M (molar) |
| Example 1 | 50 | 3.2 × $10^{-7}$ |
| Examples 2 and 3 (isomer B) | 50 | 3.5 × $10^{-8}$ |
| Example 4 | 50 | 8 × $10^{-8}$ |
| Example 5 | 50 | 7.5 × $10^{-8}$ |

TABLE II

| | % protection against bone resorption (Ca$^{++}$ release) | collagenase inhibition IC$_{50}$ (µM) |
|---|---|---|
| Inhibition (diastereo-isomers) | | |
| Example 2, isomer B, | | |

TABLE II-continued

| | % protection against bone resorption (Ca++ release) | collagenase inhibition IC50 (μM) |
|---|---|---|
| 8 μM | 90-100 | |
| Example 2, isomer B, 25 μM | 90-100 | 0.035 |
| Example 2, isomer A, 8 μM | 0 | |
| Example 2, isomer A, 25 μM | 0 | 16 |

TABLE III

SPECIFICITY OF THE INHIBITION

| | INHIBITOR (% inhibition) | | | |
|---|---|---|---|---|
| | Compound of Ex. 1 | | Compound of Ex. 2, mixture of isomers A and B | |
| ENZYME | $10^{-5}$M | $10^{-7}$M | $10^{-5}$M | $10^{-7}$M |
| Porcine collagenase | 100 | 23 | 100 | 52 |
| Human collagenase | 100 | 12 | 100 | 30 |
| ACE | 4 | 0 | 40 | 4 |
| Carboxypeptidase A | 0 | 0 | 0 | 0 |
| Carboxypeptidase B | 0 | 0 | 0 | 0 |
| α-Chymotrypsin | 0 | 0 | 0 | 0 |
| Plasmin | 0 | 0 | 0 | 0 |
| Thrombin | 0 | 0 | 5 | 0 |
| Trypsin | 0 | 0 | 0 | 0 |
| Papain | 5 | 0 | 5 | 0 |
| Pepsin | 19 | 0 | 19 | 0 |

What is claimed is:

1. Compounds with collagenase-inhibiting activity, corresponding to the general formula:

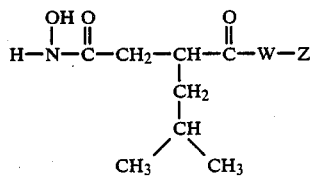

in which:
W represents an amino acid residue selected from the group consisting of valine, lysine, norleucine and methionine, and
Z represents an amino radical or an alkylamino radical of which the alkyl part, which contains 1 or 2 carbon atoms, is substituted by a phenyl or trifluorophenyl radical,
and also their diastereoisomers and their addition salts with pharmaceutically acceptable acids.

2. Compounds as claimed in claim 1 which correspond to formula I in which W represents an L-valyl group.

3. Compounds as claimed in claim 1, selected from the group comprising the following:
Nα-(N-hydroxy-2-isobutylsuccinamoyl)-L-valinamide,
N-benzyl-Nα-(N-hydroxy-2-isobutylsuccinamoyl)-L-valinamide
N-(4-trifluoromethylbenzyl)-Nα-(N-hydroxy-2-isobutylsuccinamoyl)-L-valinamide
N-phenethyl-Nα-(N-hydroxy-2-isobutylsuccinamoyl)-L-valinamide
N-benzyl-Nα-(N-hydroxy-2-isobutylsuccinamoyl)-L-norleucine and
N-benzyl-Nα-(N-hydroxy-2-isobutylsuccinamoyl)-L-lysinamide
N-benzyl-Nα-(N-hydroxy-2-isobutylsuccinamoyl)-L-methioninamide.

4. A pharmaceutical composition which contains at least a compound as claimed in one of claims 1 or 3 as the active ingredient, in association with a pharmaceutically acceptable, non-toxic vehicle or excipient.

5. A pharmaceutical composition with collagenase-inhibiting activity, which contains at least a compound as claimed in one of claims 1 or 3 as the active ingredient, in association with a pharmaceutically acceptable, non-toxic vehicle or excipient.

6. A pharmaceutical composition according to claim 5, wherein the active ingredient is in the form of the most active isomer, as determined after separation of the distinct isomeric forms of the compound.

7. A pharmaceutical composition with collagenase inhibiting activity, which contains at least one compound as claimed in claim 2, as the active ingredient, in association with a pharmaceutically acceptable, non-toxic vehicle or excipient, wherein the active ingredient is in the form of the most active isomer, as determined after separation of the distinct isomeric forms of the compound, said active isomer being characterized in NMR by the chemical shift situated at or below 2 ppm and corresponding to the >CHβ— of the valine.

8. Method of treatment of diseases which involve excessive destruction of collagen by collagenase, wherein said method comprises administering a pharmaceutical composition according to claim 5.

9. Method of treatment of diseases which involve excessive destruction of collagen by collagenase, wherein said method comprises administering a pharmaceutical composition according to claim 6.

10. Compounds as claimed in claim 1, wherein Z represents an alkylamino radical of which the alkyl part, which contains 1 or 2 carbons, is substituted by a phenyl or trifluorophenyl radical.

* * * * *